US009555115B2

(12) United States Patent
Suefuji (10) Patent No.: US 9,555,115 B2
(45) Date of Patent: Jan. 31, 2017

(54) PHARMACEUTICAL COMPOSITION FOR ORAL ADMINISTRATION WITH IMPROVED DISSOLUTION AND/OR ABSORPTION

(71) Applicant: Taiho Pharmaceutical Co., Ltd., Tokyo (JP)

(72) Inventor: Takashi Suefuji, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 46 days.

(21) Appl. No.: 14/423,750

(22) PCT Filed: Sep. 18, 2013

(86) PCT No.: PCT/JP2013/075157
§ 371 (c)(1),
(2) Date: Feb. 25, 2015

(87) PCT Pub. No.: WO2014/046129
PCT Pub. Date: Mar. 27, 2014

(65) Prior Publication Data
US 2015/0297722 A1 Oct. 22, 2015

(30) Foreign Application Priority Data

Sep. 19, 2012 (JP) ................. 2012-205681

(51) Int. Cl.
*A61K 47/12* (2006.01)
*A61K 31/5377* (2006.01)
*A61K 9/20* (2006.01)
*A61K 9/00* (2006.01)

(52) U.S. Cl.
CPC ............ *A61K 47/12* (2013.01); *A61K 9/0053* (2013.01); *A61K 9/2013* (2013.01); *A61K 31/5377* (2013.01)

(58) Field of Classification Search
None
See application file for complete search history.

(56) References Cited

U.S. PATENT DOCUMENTS

| | | | |
|---|---|---|---|
| 4,596,705 A | 6/1986 | Schepky et al. | |
| 5,942,249 A | 8/1999 | Iwao et al. | |
| 8,865,714 B2 * | 10/2014 | Urade | C07D 207/34 514/235.8 |
| 9,062,035 B2 * | 6/2015 | Urade | C07D 207/34 |
| 2004/0137052 A1 | 7/2004 | Uchiyama et al. | |
| 2005/0038077 A1 | 2/2005 | Kohlrausch | |
| 2005/0095293 A1 | 5/2005 | Brauns et al. | |
| 2010/0215750 A1 | 8/2010 | Ohta et al. | |
| 2011/0124687 A1 | 5/2011 | Hiraishi et al. | |
| 2011/0275637 A1 | 11/2011 | Chapman et al. | |
| 2011/0313609 A1 | 12/2011 | Endo et al. | |
| 2011/0319413 A1 | 12/2011 | Urade et al. | |
| 2013/0261156 A1 | 10/2013 | Hiraishi et al. | |

FOREIGN PATENT DOCUMENTS

| | | |
|---|---|---|
| CN | 102341385 A | 2/2012 |
| JP | H11106353 A | 4/1999 |
| JP | 2006028131 A | 2/2006 |
| WO | 02/087621 A1 | 11/2002 |
| WO | 2008123536 A1 | 10/2008 |
| WO | 2009147211 A1 | 12/2009 |
| WO | 2010013823 A2 | 2/2010 |

OTHER PUBLICATIONS

1-Piperazinecarbonxamide,4-[(1-methyl-1H-pyrrol-2-yl)carbonyl]-N-[4-[4-(4-(morpholinylcarbonyl)-1-piperidinyl]phenyl]-, Predicated Properties, STN Registry, Oct. 4, 2010, 3 pages.
Office Action cited in the corresponding Chinese Application No. 201380048719.6 dated Feb. 16, 2016, 7 pages.
Extended Search Report cited in European Application No. 13839200.6, dated Mar. 29, 2016, 5 pages.
Hayashi et al., "Physiological mechanism for enhancement of paracellular drug transport", Journal of Controlled Release, 62 (1999), pp. 141-148.
International Search Report cited in PCT/JP203/075157, Dec. 10, 2013, 2 pgs.

* cited by examiner

*Primary Examiner* — Samantha Shterengarts
(74) *Attorney, Agent, or Firm* — Rothwell, Figg, Ernst & Manbeck, P.C.

(57) ABSTRACT

This invention relates to a pharmaceutical composition for oral administration comprising 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof, as an active pharmaceutical ingredient; and at least one acid additive selected from the group consisting of adipic acid, succinic acid, fumaric acid, L-aspartic acid, and L-glutamic acid.

10 Claims, 3 Drawing Sheets

PHARMACEUTICAL COMPOSITION FOR ORAL ADMINISTRATION WITH IMPROVED DISSOLUTION AND/OR ABSORPTION

CROSS REFERENCE TO RELATED ART

This application is a 37 U.S.C. 371 National Phase Entry Application from PCT/JP2013/075157, filed Sep. 18, 2013, which claims priority to Japanese Patent Application No. 2012-205681 filed on Sep. 19, 2012, the disclosure of which is incorporated herein by reference in its entirety.

TECHNICAL FIELD

The present invention relates to a pharmaceutical composition for oral administration comprising 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof.

BACKGROUND ART

Bioavailability, which is an index showing the extent to which an administrated drug reaches and acts in the blood in the general circulation, is a clinically significant parameter closely relating to drug efficacy or toxicity. Prediction or control of drug efficacy or toxicity of drugs with low bioavailability is difficult because they sometimes fail to attain the expected drug efficacy or have large intra- or inter-individual variation. Thus, obtaining appropriate bioavailability is important in the development of pharmaceutical products. Orally administered drugs are affected by the gastrointestinal absorption efficiency and metabolism in the liver and gastrointestinal tract. In particular, for poorly soluble drugs, improving drug dissolution from a pharmaceutical preparation or improving drug solubility in water is important to obtain appropriate bioavailability.

4-((1-methylpyrrol-2-yl)-carbonyl)-N-(4-(4-morpholin-1-yl-carbonylpiperidin-1-yl)-phenyl)-1-piperazinecarboxamide or a salt thereof is a drug for preventing and/or treating allergy diseases, inflammatory diseases, degenerative muscle diseases and the like, caused by an inhibitory effect of prostaglandin D synthase, particularly, hematopoietic prostaglandin D synthase (Patent Literature 1). However, there has been a problem of ensuring appropriate bioavailability because of the drug's low absorption and dissolution in the neutral pH range.

To improve drug dissolution and absorption, a method of adding an organic acid is widely known. Reported techniques include, for example, a technique of combining a benzimidazole compound and a pH modifier such as monosodium fumarate (Patent Literature 2), a technique of combining a morphinan derivative and an organic acid such as fumaric acid (Patent Literature 3), and the like.

However, regarding 4-((1-methylpyrrol-2-yl)-carbonyl)-N-(4-(4-morpholin-1-yl-carbonylpiperidin-1-yl)-phenyl)-1-piperazinecarboxamide, there has been no document reporting that dissolution and/or absorption is improved by adding a specific organic acid as an acid additive, as in the present invention.

CITATION LIST

Patent Literature

PTL 1: WO2010/104024
PTL 2: WO2008/123536
PTL 3: WO2008/143240

SUMMARY OF INVENTION

Technical Problem

An object of the present invention is to provide a pharmaceutical composition for oral administration comprising 4-((1-methylpyrrol-2-yl)-carbonyl)-N-(4-(4-morpholin-1-yl-carbonylpiperidin-1-yl)-phenyl)-1-piperazinecarboxamide, the pharmaceutical composition having improved dissolution and/or absorption.

Solution to Problem

The present inventors added a different type of organic acid to 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof to evaluate its compatibility, dissolution, and absorption. As a result, they found that by adding a specific organic acid such as adipic acid, succinic acid, or fumaric acid as an acid additive, a pharmaceutical composition for oral administration with excellent dissolution and absorption can be obtained without affecting the stability of 4-((1-methylpyrrol-2-yl)-carbonyl)-N-(4-(4-morpholin-1-yl-carbonylpiperidin-1-yl)-phenyl)-1-piperazinecarboxamide. The present invention was thus accomplished.

Specifically, the present invention provides a pharmaceutical composition for oral administration comprising: 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof; and at least one organic acid selected from the group consisting of adipic acid, succinic acid, fumaric acid, L-aspartic acid, and L-glutamic acid.

Advantageous Effects of Invention

The present invention provides patients and health care professionals with a pharmaceutical composition for oral administration having excellent dissolution and absorption since the stability of the active pharmaceutical ingredient is not adversely affected and the pharmaceutical composition ensures its stability.

DESCRIPTION OF EMBODIMENTS

As used throughout this disclosure, the singular forms "a," "an," and "the" include both the singular and the plural unless otherwise indicated herein or clearly contradicted by context.

The active pharmaceutical ingredient of the pharmaceutical composition for oral administration of the present invention is 4-((1-methylpyrrol-2-yl)-carbonyl)-N-(4-(4- morpholin-1-yl-carbonylpiperidin-1-yl)-phenyl)-1-piperazinecarboxamide. 4-((1-methylpyrrol-2-yl)-carbonyl)-N-(4-(4-morpholin-1-yl-carbonylpiperidin-1-yl)-phenyl)-1-piperazinecarboxamide may be a salt. Examples of the salt of the compound of the present invention include salts conventionally used in the field of organic chemistry, such as acid addition salts.

Examples of the acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; sulfonates such as methanesulfonates, isethionates, benzenesulfonates, and p-toluenesulfonates; etc.

4-((1-methylpyrrol-2-yl)-carbonyl)-N-(4-(4-morpholin-1-yl-carbonylpiperidin-1-yl)-phenyl)-1-piperazinecarboxamide may be a solvate, preferably hydrate, and more preferably monohydrate.

The pharmaceutical composition for oral administration of the present invention includes an acid additive. The acid additive is adipic acid, succinic acid, fumaric acid, L-aspartic acid, or L-glutamic acid. These acid additives can be used singly or in a combination of two or more.

The amount of the acid additive to be mixed is about 0.25 to 5 parts by mass, preferably about 0.5 to 2 parts by mass, more preferably about 0.8 to 1.5 parts by mass, and most preferably about 1 part by mass per part by mass of the active pharmaceutical ingredient 4-(1-methylpyrrol-2-yl)-carbonyl)-N-(4-(4-morpholin-1-yl-carbonylpiperidin-1-yl)-phenyl)-1-piperazinecarboxamide. When two or more acid additives are added, the total amount of the acid additives is considered to be the amount of the acid additive.

The pharmaceutical composition for oral administration of the present invention may include various excipients that are generally used for pharmaceutical preparations as long as the effect of the present invention is not impaired. The excipients for pharmaceutical preparations are not particularly limited as long as they are excipients generally used. Examples of such excipients include diluents, binders, disintegrants, lubricants, flavors, coating agents, coloring agents, corrigents and the like.

When a diluent is contained as an excipient, the amount of the acid additive to be mixed is about 0.15 to 6 parts by mass, preferably about 0.2 to 2 parts by mass, and more preferably about 0.5 to 2 parts by mass per part by mass of the diluting agent. When two or more acid additives are used, the total amount of the acid additives is considered to be the amount of the acid additive.

Examples of the diluents include lactose, saccharose, sucrose, mannitol, crystalline cellulose, corn starch, dextran and the like. Examples of the binders include hydroxypropyl cellulose, hypromellose, polyvinyl alcohol and the like. Examples of the disintegrants include croscarmellose sodium, crospovidone, low-substituted hydroxypropyl cellulose and the like. Examples of the lubricants include hydrogenated oil, magnesium stearate, calcium stearate, talc, sucrose esters of fatty acids, and stearic acid. Examples of the coating agents include ethyl cellulose, hypromellose, hypromellose phthalic acid ester, macrogol, Opadry and the like. Examples of the coloring agents include food yellow No. 5, food blue No. 2, food lake dye, ferric oxide, yellow ferric oxide, titanium oxide and the like. Examples of the flavors include various fragrances of orange, lemon and the like. Examples of the corrigents include 1-menthol, camphor, peppermint and the like. These can be used singly or in a combination of two or more.

The pharmaceutical composition for oral administration of the present invention can be formed into granulated products, compression-molded products (e.g., uncoated tablets and film-coated tablets), powders and the like. The pharmaceutical preparation for oral administration of the present invention may be formed into tablets, granules, powders, fine granules and the like. Examples of the tablets include chewable tablets, troches, drops, tablets which quickly dissolve or disintegrate in the oral cavity and can be taken without water, and effervescent tablets that dissolve when used. Examples of the granules, powders, and fine granules include dry syrups that dissolve when used, and powdery or granular products that quickly dissolve in the oral cavity and can be taken without water.

The pharmaceutical composition or pharmaceutical preparation for oral administration of the present invention can be produced by using a known method for producing orally administered pharmaceutical preparations. Examples of the method include a directly tableting method in which components are mixed, followed by tableting and a method in which a granulated product containing components is produced, followed by tableting. Examples of the granulation method include fluid bed granulation, agitation granulation, fluid bed rotation granulation, extrusion granulation, spray granulation, crushing granulation and the like. The resulting tablets may be film-coated, for example, by spraying a coating liquid onto the tablets.

The composition of the present invention is administered to mammals such as humans, monkeys, dogs, cats, rabbits, mice, rats, and guinea pigs, and preferably to humans.

The daily dose of the pharmaceutical composition for oral administration of the present invention can be suitably selected according to the patient's condition, age, body weight, and sex, administration method, or the like. The daily dose of the 4-((1-methylpyrrol-2-yl)-carbonyl)-N-(4-(4-morpholin-1-yl-carbonylpiperidin-1-yl)-phenyl)-1-piperazinecarboxamide, which is contained as an active pharmaceutical ingredient, for an adult (body weight: 50 kg) is typically about 1 to 1,000 mg, and preferably 10 to 800 mg. The composition can be administered in a single dose or in about two to three divided doses per day.

In one embodiment, active pharmaceutical ingredient compound 1, a salt thereof, or a solvate thereof in the composition of the present invention is stabilized. The expression "stabilized" indicates that the decomposition amount of compound 1 monohydrate obtained when a mixed powder of active pharmaceutical ingredient compound 1 and an acid additive is allowed to stand for a specific period (e.g., two weeks) is smaller than the amount obtained when no acid additive is added.

In another embodiment, the composition of the present invention has improved dissolution. The expression "improved dissolution" herein indicates that the pharmaceutical composition or preparation containing an acid additive according to the present invention has equivalent dissolution to or higher than the dissolution of a pharmaceutical composition or preparation containing no acid additive. One example is a case where a difference in dissolution between an active pharmaceutical ingredient in a pharmaceutical preparation containing an acid additive and an active pharmaceutical ingredient in a pharmaceutical preparation containing no acid additive is above 10%, wherein both preparations are obtained 15 minutes after a dissolution test, which is performed according to the dissolution test (specifically, a paddle method) described in the Japanese Pharmacopoeia, Sixteenth Edition.

In still another embodiment, the composition of the present invention can attain improved absorption. The expression "improved absorption" herein indicates that the body absorption of the pharmaceutical composition or preparation containing an acid additive according to the present invention is equivalent to or higher than the absorption of a pharmaceutical composition or preparation that does not contain an acid additive. For example, the area under the blood concentration-time curve (AUC) obtained after the administration of the pharmaceutical composition or preparation of the present invention is 1.5 or more times larger than that of a pharmaceutical preparation that does not contain an acid additive. Additionally, the maximum drug concentration (Cmax) of the active pharmaceutical ingredient obtained after the administration of the pharmaceutical composition or preparation of the present invention is 1.5 or more times larger than that of a pharmaceutical preparation containing no acid additive.

Below are shown the embodiments, including preferable embodiments, of the present invention.

1. A pharmaceutical composition for oral administration comprising 4-((1-methylpyrrol-2-yl)-carbonyl)-N-(4-(4-morpholin-1-ylcarbonylpiperidin-1-yl)-phenyl)-1-piperazinecarboxamide, a salt thereof, or a solvate thereof, as an active pharmaceutical ingredient; and at least one acid additive selected from the group consisting of adipic acid, succinic acid, fumaric acid, L-aspartic acid, and L-glutamic acid.

2. The pharmaceutical composition for oral administration according to Item 1, wherein the acid additive is contained in an amount of 0.25 to 5 parts by mass per part by mass of the 4-((1-methylpyrrol-2-yl)-carbonyl)-N-(4-(4-morpholin-1-yl-carbonylpiperidin-1-yl)-phenyl)-1-piperazinecarboxamide.

3. The pharmaceutical composition for oral administration according to Item 1, wherein the acid additive is contained in an amount of 0.5 to 2 parts by mass per part by mass of the 4-((1-methylpyrrol-2-yl)-carbonyl)-N-(4-(4-morpholin-1-yl-carbonylpiperidin-1-yl)-phenyl)-1-piperazinecarboxamide.

4. The pharmaceutical composition for oral administration according to Item 1, wherein the composition further comprises a diluent, and the acid additive is contained in an amount of 0.15 to 6 parts by mass per part by mass of the diluent.

5. The pharmaceutical composition for oral administration according to any one of Items 1 to 4, wherein the acid additive is fumaric acid.

6. The pharmaceutical composition according to any one of Items 1 to 5, wherein a difference in dissolution rate between an active pharmaceutical ingredient of a pharmaceutical preparation containing an acid additive and an active pharmaceutical ingredient of a pharmaceutical preparation containing no acid additive is above 10%, the pharmaceutical preparations being obtained 15 minutes after a dissolution test according to a dissolution test method described in the Japanese Pharmacopoeia, Sixteenth Edition.

7. The pharmaceutical composition for oral administration according to any one of Items 1 to 5, wherein the AUC and Cmax of the active pharmaceutical ingredient obtained after oral administration of the pharmaceutical composition are 1.5 or more times larger than the AUC and Cmax of the pharmaceutical composition containing no acid additive.

8. A method for stabilizing 4-((1-methylpyrrol-2-yl)-carbonyl)-N-(4-(4-morpholin-1-ylcarbonylpiperidin-1-yl)-phenyl)-1-piperazinecarboxamide, a salt thereof, or a solvate thereof contained in a pharmaceutical composition, the method comprising adding at least one acid additive selected from the group consisting of adipic acid, succinic acid, fumaric acid, L-aspartic acid, and L-glutamic acid to the pharmaceutical composition.

9. A method for improving dissolution of 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition, the method comprising adding at least one acid additive selected from the group consisting of adipic acid, succinic acid, fumaric acid, L-aspartic acid, and L-glutamic acid to the pharmaceutical composition.

10. A method for improving absorption of 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition, the method comprising adding at least one acid additive selected from the group consisting of adipic acid, succinic acid, fumaric acid, L-aspartic acid, and L-glutamic acid to the pharmaceutical composition.

11. Use of at least one acid additive selected from the group consisting of adipic acid, succinic acid, fumaric acid, L-aspartic acid, and L-glutamic acid for stabilizing 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition.

12. Use of at least one acid additive selected from the group consisting of adipic acid, succinic acid, fumaric acid, L-aspartic acid, and L-glutamic acid for improving dissolution of 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition.

13. Use of at least one acid additive selected from the group consisting of adipic acid, succinic acid, fumaric acid, L-aspartic acid, and L-glutamic acid for improving absorption of 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition.

14. Use of at least one acid additive selected from the group consisting of adipic acid, succinic acid, fumaric acid, L-aspartic acid, and L-glutamic acid for producing a pharmaceutical composition for oral administration comprising 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof.

EXAMPLES

The present invention is explained in detail with reference to the Examples; however, the present invention is not limited to these.

In Examples 2 to 5, the following materials can be used: a diluent selected from lactose, saccharose, sucrose, mannitol, crystalline cellulose, corn starch, and dextran; a binder selected from hydroxypropyl cellulose, hypromellose, and polyvinyl alcohol; a disintegrant selected from croscarmellose sodium, crospovidone, and low-substituted hydroxypropyl cellulose; a lubricant selected from hydrogenated oil, magnesium stearate, calcium stearate, talc, sucrose fatty acid ester, and stearic acid; a coating agent selected from ethyl cellulose, hypromellose, hypromellose phthalic acid ester, macrogol, and Opadry; and a coloring agent selected from food yellow No. 5, food blue No. 2, food lake dye, ferric oxide, yellow ferric oxide, and titanium oxide. No diluent, binder, disintegrant, lubricant, coating agent, or coloring agent will substantially affect the evaluation of dissolution or absorption of the pharmaceutical preparations.

Example 1

Compatibility Test 4-((1-methylpyrrol-2-yl)-carbonyl)-N-(4-(4-morpholin-1-yl-carbonylpiperidin-1-yl)-phenyl)-1-piperazinecarbox-amide (compound 1) monohydrate and organic acids were respectively weighed in an amount of 0.5 g. Compound 1 monohydrate was mixed with each organic acid in a mortar to produce individual mixed powders. Subsequently, compound 1 monohydrate alone was weighed in an amount of 0.5 g to produce a compound 1 monohydrate powder according to the same method as in the production of the organic acid mixed powders.

Each organic acid mixed powder and each compound 1 monohydrate powder were weighed in amounts of 0.04 g and 0.02 g, respectively, in sealed and open glass bottles. These bottles were allowed to stand at 60° C. and a relative humidity of 60% for two weeks, and then the production of a compound 1 monohydrate related substance was examined by HPLC to evaluate stability. In the evaluation, a high-speed liquid chromatograph (Shimadzu Corporation) was used. Table 2 shows the results.

Test Conditions

Detector: Ultraviolet spectrophotometer (measurement wavelength: 260 nm)

Column: Phenylated silica gel for liquid chromatography (3.5 μm) (XBridge Phenyl, Japan Waters, Inc.) was placed in a stainless pipe with an inner diameter of 4.6 mm and a length of 10 cm.

Column temperature: Constant temperature of around 40° C.

Mobile Phase

Mobile phase A: Phosphate buffer solution (pH 7)

Mobile phase B: Acetonitrile

Transfer of mobile phase: The concentration gradient is regulated by changing the mixing ratio of mobile phases A and B as shown in Table 1.

TABLE 1

| Mixing Ratio of Phases A and B | | |
|---|---|---|
| Time after injection (min) | Phase A (%) | Phase B (%) |
| 0-2 | 90->80 | 10->20 |
| 2-15 | 80->75 | 20->25 |
| 15-20 | 75->30 | 25->70 |
| 20-22 | 30 | 70 |

Flow rate: 1.5 mL/min

When anhydrous citric acid, L-tartaric acid, DL-tartaric acid, or DL-malic acid was added as an acid additive, the amount of a related substance significantly increased under open conditions, sealed conditions, or both. In contrast, when an organic acid selected from adipic acid, succinic acid, fumaric acid, L-aspartic acid, and L-glutamic acid was added, the amount of an related substance was the same as the initial value under both open conditions and sealed conditions, which did not affect the stability of compound 1 (Table 2).

TABLE 2

| | Sealed Related Substances (mass %) | Open Related Substances (mass %) | Initial value Related Substances (mass %) |
|---|---|---|---|
| Compound 1 monohydrate | 0.44 | 0.47 | 0.46 |
| +adipic acid | 0.20 | 0.17 | 0.23 |
| +succinic acid | 0.21 | 0.26 | 0.20 |
| +fumaric acid | 0.26 | 0.25 | 0.25 |
| +L-aspartic acid | 0.19 | 0.18 | 0.21 |
| +L-glutamic acid | 0.20 | 0.17 | 0.20 |
| +anhydrous citric acid | 2.03 | 43.31 | 0.50 |
| +L-tartaric acid | 0.69 | 45.62 | 0.38 |
| +DL-tartaric acid | 0.73 | 35.39 | 0.76 |
| +DL-malic acid | 29.60 | 60.90 | 0.37 |

Example 2

Evaluation of Dissolution of Pharmaceutical Preparation Containing Organic Acid Tablets of Formulation Example 1, Formulation Example 2, and Comparative Example 1 were produced. Table 3 shows the formulation of each tablet.

Formulation Example 1

Compound 1 monohydrate (1 g), and fumaric acid (1 g) as an acid additive were placed in a tablet grinder (Konishi Seisakusyo Co., Ltd.) and milled to obtain a milled product containing fumaric acid. The milled product containing fumaric acid (1.50 g), a diluent (4.17 g), a disintegrant (0.30 g), and a lubricant (0.030 g) were introduced and mixed in a glass bottle, and then the mixture was compressed using a tableting machine to obtain tablets each weighing 200 mg.

Formulation Example 2

Succinic acid (1 g) was added as an acid additive in place of the fumaric acid (1 g) of Formulation Example 1, followed by milling to obtain a milled product containing succinic acid. Tablets each weighing 200 mg were obtained in the same manner as in Formulation Example 1.

Comparative Example 1

As a control, tablets were obtained in the same manner as in Formulation Examples 1 and 2 except that no acid additive was added.

Dissolution Test

Regarding Formulation Examples 1 and 2, and Comparative Example 1, the dissolution test was performed at 50 rpm using 900 mL of dissolution test solution 2 (37° C.) as a test solution in accordance with the paddle method of the dissolution test methods described in the Japanese Pharmacopoeia, Sixteenth Edition. As measurement equipment, a dissolution tester (Toyama Sangyo Co., Ltd.) and a solution monitor (Otsuka Electronics Co., Ltd.) were used.

Figure 1:
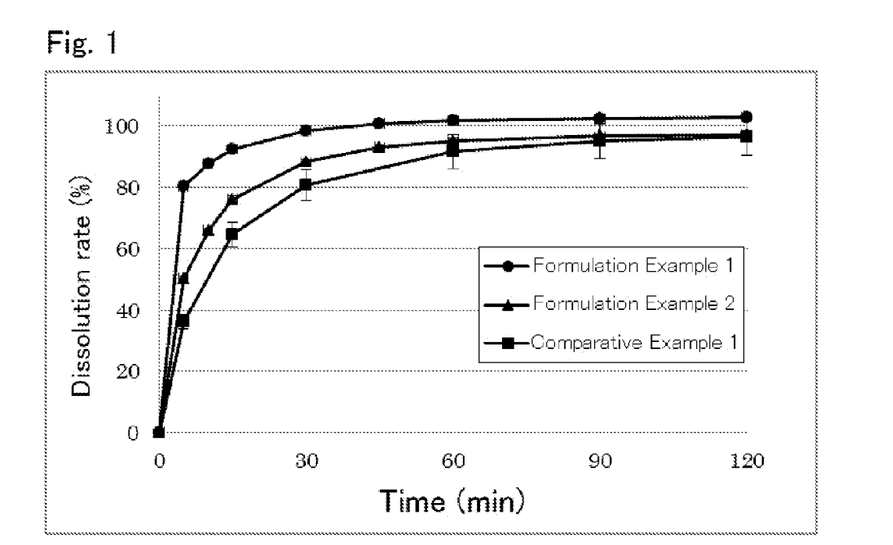
FIG. 1 shows the results of the dissolution test in Example 2.

The results are shown in FIG. 1 (n=3, average dissolution rate±SD). In Comparative Example 1, which contained no acid additive, the dissolution rate obtained 15 minutes later was 65%, whereas in Formulation Example 1, which contained fumaric acid, and Formulation Example 2, which contained succinic acid, the dissolution rates obtained 15 minutes later were 93% and 76%, respectively. This confirmed that the acid additives of the present invention had a dissolution improvement effect.

TABLE 3

|  | Formulation Example 1 (mg/tablet) | Formulation Example 2 (mg/tablet) | Comparative Example 1 (mg/tablet) |
|---|---|---|---|
| Compound 1 monohydrate | 25 | 25 | 25 |
| Fumaric acid | 25 | — | — |
| Succinic acid | — | 25 | — |
| Diluent | 139 | 139 | 139 |
| Disintegrant | 10 | 10 | 10 |
| Lubricant | 1 | 1 | 1 |
| Total | 200 | 200 | 175 |

Example 3

Evaluation of Dissolution of Pharmaceutical Preparation Containing Fumaric Acid

Tablets of Formulation Examples 3, 4, 5, and 6, and Comparative Example 2 were produced. Table 4 shows the formulation of each tablet.

Formulation Example 3

Compound 1 monohydrate, fumaric acid, and a diluent were placed in a fluidized bed granulator (Powrex Corp.), and the mixture was granulated with spraying a binder solution to obtain a granulated product. A disintegrant and a lubricant were added to the resulting granulated product and mixed, and then the mixture was compressed by using a tableting machine (Kikusui Seisakusyo Ltd.) to obtain tablets each weighing 282 mg. A film coating liquid comprising a coating agent, coloring agent, and purified water (about 92% relative to the coating solution) was sprayed onto the resulting tablets using a coater (Powrex Corp.) to obtain film-coated tablets each weighing 296 mg. In Formulation Example 3, the amount of fumaric acid was about 0.25 parts by mass per part by mass of the compound 1 monohydrate.

Formulation Example 4

Film-coated tablets were obtained in the same manner as in Formulation Example 3 except that the amount of fumaric acid was changed to about 0.5 per part by mass of the compound 1 monohydrate, and the mixing ratio of the fumaric acid and the diluent was changed.

Formulation Example 5

Film-coated tablets each weighing 296 mg were obtained in the same manner as in Formulation Example 3 except that the amount of fumaric acid was changed to about 0.8 per part by mass of the compound 1 monohydrate, and the mixing ratio of the fumaric acid and the diluent was changed.

Formulation Example 6

Film-coated tablets each weighing 296 mg were obtained in the same manner as in Formulation Example 3 except that the amount of fumaric acid was changed to about 1.0 per part by mass of the compound 1 monohydrate, and the mixing ratio of the fumaric acid and the diluent was changed.

Comparative Example 2

Figure 2:
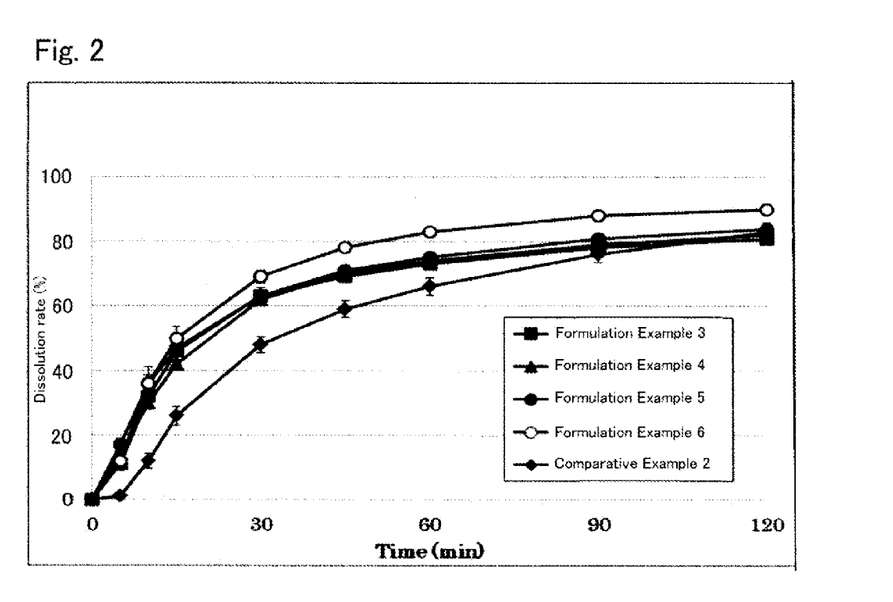
FIG. 2 shows the results of the dissolution test in Example 3.

As a control, film-coated tablets each weighing 296 mg were obtained in the same manner as in Formulation Example 3 except that no fumaric acid was added and that the mixing ratio of the diluent was changed.
Dissolution Test Regarding Formulation Examples 3, 4, 5, and 6, and Comparative Example 2, the dissolution test was performed at 50 rpm using 900 mL of dissolution test solution 2 (37° C.) as a test solution in accordance with the paddle method of the dissolution test methods described in the Japanese Pharmacopoeia, Sixteenth Edition. In the evaluation, a high-speed liquid chromatograph (Shimadzu Corporation) was used. The results are shown in FIG. 2 (n=3, average dissolution rate±SD). Formulation Examples 3, 4, 5, and 6, which contained fumaric acid, showed improvement in dissolution compared to Comparative Example 2, which contained no fumaric acid.

TABLE 4

|  | Formulation Example 3 (mg/tablet) | Formulation Example 4 (mg/tablet) | Formulation Example 5 (mg/tablet) | Formulation Example 6 (mg/tablet) | Comparative Example 2 (mg/tablet) |
|---|---|---|---|---|---|
| Compound 1 monohydrate | 104 | 104 | 104 | 104 | 104 |
| Fumaric acid | 25 | 50 | 80 | 100 | 0 |
| Diluent | 125 | 100 | 70 | 50 | 150 |
| Binder | 10 | 10 | 10 | 10 | 10 |
| Disintegrant | 15 | 15 | 15 | 15 | 15 |
| Lubricant | 3 | 3 | 3 | 3 | 3 |
| Coating agent | 12.6 | 12.6 | 12.6 | 12.6 | 12.6 |
| Coloring agent | 1.54 | 1.54 | 1.54 | 1.54 | 1.54 |
| Total | 296 | 296 | 296 | 296 | 296 |

Example 4

Evaluation of Absorption of Pharmaceutical Preparation Containing Fumaric Acid

Tablets of Formulation Example 7 and Comparative Example 3 were produced. Table 6 shows the formulation of each tablet.

Formulation Example 7

Compound 1 monohydrate (2.40 g), fumaric acid (2.40 g), and a diluent (1.2 g) were placed in a mortar. A binder solution (1.28 g) was added thereto, and the mixture was granulated to obtain a granulated product. The granulated product was sized, and then allowed to stand and dried at 60° C. for one hour to obtain a dry granulated product. A disintegrant (0.26 g) and a lubricant (0.02 g) were added to the resulting dry granulated product (5.08 g) and mixed. The mixture was then compressed using a tableting machine (Shimadzu Corporation) to obtain tablets each weighing 268 mg.

Comparative Example 3

As a control, tablets each weighing 268 mg were obtained in the same manner as in Formulation Example 7 except that the granulated product was obtained by adding no fumaric acid and increasing the amount of the diluent to 3.60 g.
Absorption Experiment Conditions
Animals used: Beagles (Kitayama Labes, male, n=6)
Meal conditions: Fasted from the previous day for 20 hours.
Dose: 100 mg/body
Sample to be administered: Formulation Example 7 and Comparative Example 3, one tablet per Example
Administration method: Administered together with 50 mL water.
Pretreatment: An atropine sulfate intravenous injection (10 μg/0.1 mL/kg) and an omeprazole intravenous injection (1 mg/0.25 mL/kg) were intravenously administered 30 minutes before sample administration. Another omeprazole intravenous injection (1 mg/0.25 mL/kg) was intravenously administered 30 minutes after the sample administration.
Method for Measuring Absorption
Blood extracted from each dog was centrifuged (12,000 rpm, 5° C., three minutes), and the resulting plasma (25 μL) was extracted in a polypropylene microtube, followed by the addition of purified water (25 μL). Acetonitrile (100 μL) and an inner standard solution (50 μL) were added and mixed in a vortex mixer. After centrifugal separation (15,000×g, 5° C., two minutes), a supernant (60 μL) was extracted in a polypropylene autosampler tube, and purified water (120 μL) was added thereto and mixed by using a vortex mixer. The resulting sample for the measurement was quantified by using a high-speed liquid chromatograph/mass spectrometer (Japan Waters, Inc.).
Device: High-speed liquid chromatograph/mass spectrometer (Japan Waters, Inc.)
Liquid Chromatography Measurement Conditions
Column: ACQUITY UPLC BEH C18 (1.7 inner diameter: 2.1 mm, length: 50 mm)
Column temperature: 40° C.
Mobile Phase
Mobile phase A: 10 mmol/L ammonium formate
Mobile phase B: Acetonitrile
Transfer of mobile phase: The concentration gradient is regulated by changing the mixing ratio of mobile phases A and B as shown in Table 5.

TABLE 5

Mixing Ratio of Phases A and B

| Time after injection (min) | Phase A (%) | Phase B (%) |
|---|---|---|
| 0.00-2.10 | 80->50 | 20->50 |
| 2.10-2.40 | 50 | 50 |
| 2.40-2.41 | 50->80 | 50->20 |
| 2.41-3.50 | 80 | 20 |

Figure 3:
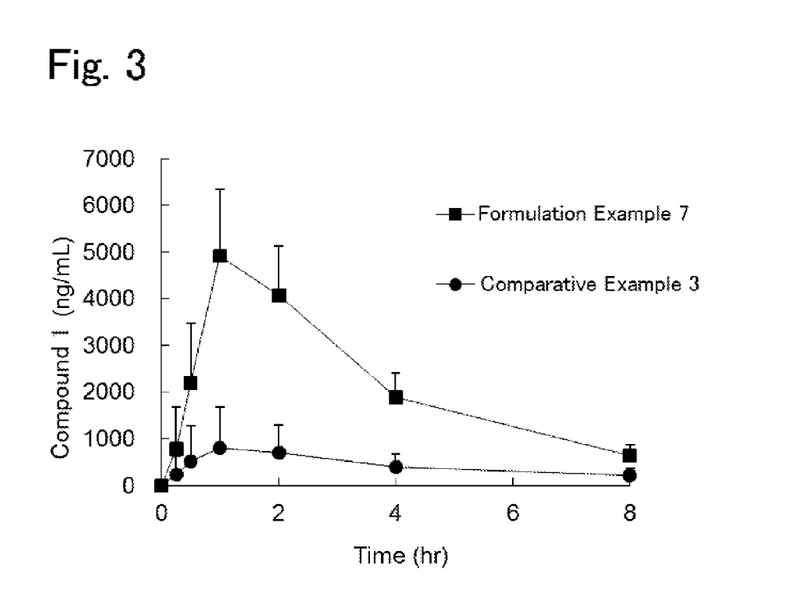
FIG. 3 shows the results of the absorption test in Example 4.

Flow rate: 0.3 mL/min
MS/MS Measurement Conditions
Ionization source: Electrospray ionization (ESI) positive mode Scan mode: MRM The results are shown in FIG. 3 (n=6, average plasma concentration+SD). The AUC (17,783±3,813) and Cmax (5,067±1,334) of Formulation Example 7, which contained fumaric acid, were respectively 5 times and 6 times larger than the AUC (3,518±2,932) and Cmax (842±850) of Comparative Example 3, which contained no fumaric acid. Formulation Example 7, which contained fumaric acid, showed improvement in absorption compared to Comparative Example 3, which contained no fumaric acid. This confirmed that fumaric acid improved absorption.

TABLE 6

|  | Formulation Example 7 (mg/tablet) | Comparative Example 3 (mg/tablet) |
|---|---|---|
| Compound 1 monohydrate | 100 | 100 |
| Fumaric acid | 100 | — |
| Diluent | 50 | 150 |
| Binder | 4 | 4 |
| Disintegrant | 13 | 13 |
| Lubricant | 1 | 1 |
| Total | 268 | 268 |

Example 5

Evaluation of Absorption of Pharmaceutical Preparation Having Different Fumaric Acid Concentration Tablets of Formulation Examples 8 and 9 were produced. Table 8 shows the formulation of each tablet.

Formulation Example 8

Compound 1 monohydrate (42.5 g), fumaric acid (40.9 g), and a diluent (204.4 g) were placed in a fluidized bed granulator (Freund Corp.), and the mixture was granulated with spraying a binder solution (123.0 g) to obtain a granulated product. A disintegrant (13.6 g) and a lubricant (1.7 g) were added to the resulting granulated product and mixed, and then the mixture was compressed by using a tableting machine (Kikusui Seisakusyo Ltd.) to obtain tablets each weighing 77.9 mg. A film coating liquid comprising a coating agent (27.0 g), a coloring agent (3.0 g), and purified water (270.0 g) was sprayed onto the resulting tablets using a coater (Powrex Corp.) to obtain film-coated tablets.

Formulation Example 9

A binder solution (108.1 g) was added to the mixture of Compound 1 monohydrate (37.4 g), fumaric acid (71.9 g), and a diluent (179.9 g), and the resulting mixture was granulated to obtain a granulated product. A disintegrant (12.0 g) and a lubricant (1.5 g) were added to the resulting granulated product (250.2 g), and the mixture was compressed by using a tableting machine (Kikusui Seisakusyo Ltd.) to obtain tablets each weighing 87.9 mg. A film coating liquid comprising a coating agent (45.0 g), a coloring agent (5.0 g), and purified water (450.0 g) was sprayed onto the resulting tablets using a coater (Powrex Corp.) to obtain film-coated tablets.

Absorption Experiment Conditions
Animals used: Beagles (Kitayama Labes, male, n=3 or 6)
Meal conditions: Fasted from the previous day for 20 hours.
Dose: 10 mg/body or 100 mg/body
Sample to be administered: Formulation Example 8 or 9, or Formulation Example 4, 5, or 6, or Comparative Example 3, one tablet per Example
Administration method: Administered together with 50 mL water Pretreatment: An atropine sulfate intravenous injection (10 μg/0.1 mL/kg) and an omeprazole intravenous injection (1 mg/0.25 mL/kg) were intravenously administered 30 minutes before sample administration. Another omeprazole intravenous injection (1 mg/0.25 mL/kg) was intravenously administered 30 minutes after sample administration.
Method for Measuring Absorption Blood extracted from each dog was centrifuged (12,000 rpm, 5° C., three minutes), and the resulting plasma (25 μL) was extracted in a polypropylene micro tube, followed by addition of purified water (25 μL). Acetonitrile (100 μL) and an inner standard solution (50 μL) were added and mixed in a vortex mixer. After centrifugal separation (15,000×g, 5° C., two minutes), a supernant (60 μL) was extracted in a polypropylene autosampler tube, and purified water (120 μL) was added thereto and mixed by using a vortex mixer. The resulting sample for the measurement was quantified by using a high-speed liquid chromatograph/mass spectrometer (Japan Waters, Inc.).
Device: High-speed liquid chromatograph/mass spectrometer (Japan Waters, Inc.)
Liquid Chromatography Measurement Conditions
Column: ACQUITY UPLC BEH C18 (1.7 inner diameter: 2.1 mm, length: 50 mm)
Column temperature: 40° C.
Mobile Phase
Mobile phase A: 10 mmol/L ammonium acetate
Mobile phase B: Acetonitrile
Transfer of mobile phase: The concentration gradient is regulated by changing the mixing ratio of mobile phases A and B as shown in Table 7.

TABLE 7

| Mixing Ratio of Phases A and B | | |
|---|---|---|
| Time after injection (min) | Phase A (%) | Phase B (%) |
| 0.00-2.25 | 80->50 | 20->50 |
| 2.25-3.00 | 50 | 50 |
| 3.00-3.01 | 50->80 | 50->20 |
| 3.01-4.50 | 80 | 20 |

Figure 4:
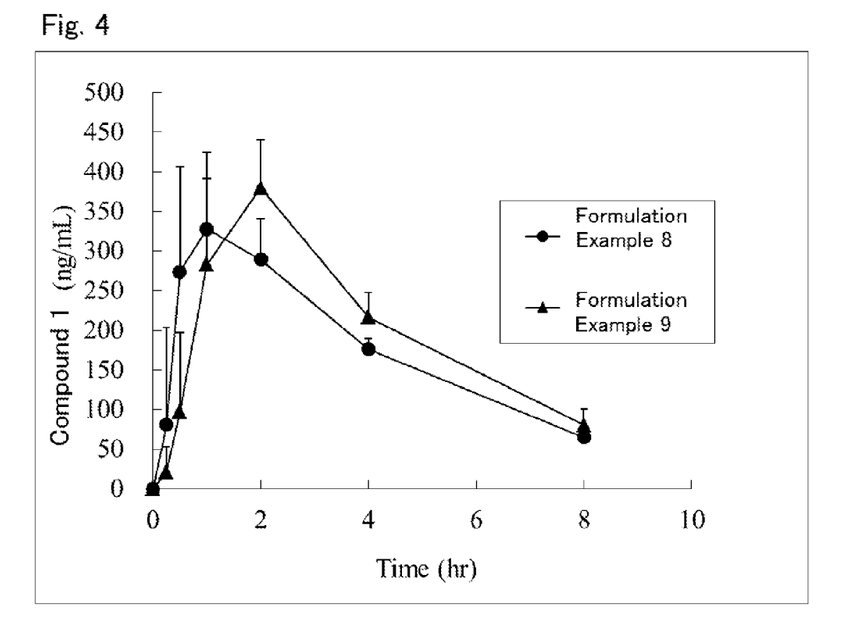
FIG. 4 shows the results of the absorption test in Example 5.
Figure 5:
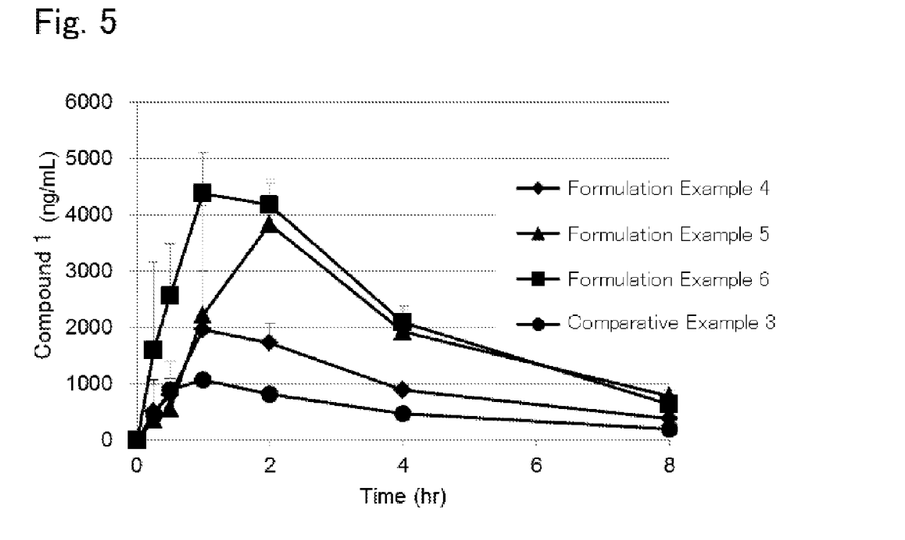
FIG. 5 shows the results of the absorption test in Example 5.

Flow rate: 0.3 mL/min
MS/MS Measurement Conditions
Ionization source: Electrospray ionization (ESI) positive mode
Scan mode: MRM The results are shown in FIG. 4 (n=6, average plasma concentration+SD) and FIG. 5 (n=3, average plasma concentration+SD). FIG. 4 shows that Formulation Example 8, which contained 1 part by mass of fumaric acid relative to compound 1, and Formulation Example 9, which contained two parts by mass of fumaric acid relative to compound 1, had sufficient absorption. The results of FIG. 5 also indicate that the AUC (7,890±1,513, 15,033±1,250, 20,324±2,856) and Cmax (2,073±922, 4,230±540, 5,023±1,258) of Formulation Examples 4, 5, and 6 were both 1.5 or more times larger than the AUC (3,518±2,932) and Cmax (842±850) of Comparative Example 3. Formulation Examples 4, 5, and 6, which contained fumaric acid, showed more excellent absorption than that of Comparative Example 3.

TABLE 8

|  | Formulation Example 8 (mg/tablet) | Formulation Example 9 (mg/tablet) |
|---|---|---|
| Compound 1 monohydrate | 10.4 | 10.4 |
| Fumaric acid | 10 | 20 |
| Diluent | 50 | 50 |
| Binder | 3 | 3 |
| Disintegrant | 4 | 4 |
| Lubricant | 0.5 | 0.5 |
| Coating agent | 3.5 | 3.95 |
| Coloring agent | 0.4 | 0.45 |
| Total | 81.8 | 92.3 |

The invention claimed is:

1. A pharmaceutical composition for oral administration comprising:
    4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof, as an active pharmaceutical ingredient; and fumaric acid.

2. The pharmaceutical composition for oral administration according to claim 1, wherein the fumaric acid is contained in an amount of 0.25 to 5 parts by mass per part by mass of the 4-((1-methylpyrrol-2-yl)-carbonyl)-N-(4-(4-morpholin-1-yl-carbonylpiperidin-1-yl)-phenyl)-1-piperazinecarboxamide.

3. The pharmaceutical composition for oral administration according to claim 1, wherein the fumaric acid is contained in an amount of 0.5 to 2 parts by mass per part by mass of the 4-((1-methylpyrrol-2-yl)-carbonyl)-N-(4-(4-morpholin-1-yl-carbonylpiperidin-1-yl)-phenyl)-1-piperazinecarboxamide.

4. The pharmaceutical composition for oral administration according to claim 1, wherein the composition further comprises a diluting agent, and the fumaric acid is contained in an amount of 0.15 to 6 parts by mass per part by mass of the diluent.

5. The pharmaceutical composition according to claim 1, wherein a difference in dissolution rate between an active pharmaceutical ingredient of a pharmaceutical preparation containing fumaric acid and an active pharmaceutical ingredient of a pharmaceutical preparation containing no fumaric acid is above 10%, the pharmaceutical preparations being obtained 15 minutes after a dissolution test according to a paddle method dissolution test.

6. The pharmaceutical composition for oral administration according to claim 1, wherein the AUC and Cmax of the active pharmaceutical ingredient obtained after oral administration of the pharmaceutical composition are 1.5 or more times larger than the AUC and Cmax of the pharmaceutical composition containing no fumaric acid.

7. A method for stabilizing 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition, the method comprising
    adding fumaric acid to the pharmaceutical composition.

8. A method for improving dissolution of 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition, the method comprising adding fumaric acid to the pharmaceutical composition.

9. A method for improving absorption of 4-((1-methyl-pyrrol-2-yl)-carbonyl)-N-(4-(4-morpholin-1-yl-carbonylpiperidin-1-yl)-phenyl)-1-piperazinecarboxamide, a salt thereof, or a solvate thereof contained in a pharmaceutical composition, the method comprising adding fumaric acid to the pharmaceutical composition.

10. A method for producing a pharmaceutical composition for oral administration comprising combining 4-((1-methylpyrrol-2-yl)-carbonyl)-N-(4-(4-morpholin-1-yl-carbonylpiperidin-1-yl)-phenyl)-1-piperazinecarboxamide, a salt thereof, or a solvate thereof, with fumaric acid.

* * * * *